US010856907B2

(12) United States Patent
Virden

(10) Patent No.: US 10,856,907 B2
(45) Date of Patent: Dec. 8, 2020

(54) ATRAUMATIC TROCAR MEDICATION DELIVERY METHOD

(71) Applicant: Charles P. Virden, Reno, NV (US)

(72) Inventor: Charles P. Virden, Reno, NV (US)

( * ) Notice: Subject to any disclaimer, the term of this patent is extended or adjusted under 35 U.S.C. 154(b) by 66 days.

(21) Appl. No.: 15/901,837

(22) Filed: Feb. 21, 2018

(65) Prior Publication Data

US 2019/0254707 A1    Aug. 22, 2019

(51) Int. Cl.
 *A61B 17/34* (2006.01)
 *A61M 31/00* (2006.01)

(52) U.S. Cl.
 CPC ...... *A61B 17/3496* (2013.01); *A61B 17/3468* (2013.01); *A61M 31/002* (2013.01); *A61M 31/007* (2013.01); *A61B 17/3421* (2013.01); *A61B 2017/3456* (2013.01)

(58) Field of Classification Search
 CPC ............ A61B 17/3468; A61B 17/3496; A61B 2017/3456; A61M 37/0069; A61M 31/002; A61M 31/007
 See application file for complete search history.

(56) References Cited

U.S. PATENT DOCUMENTS

| 3,921,632 A | 11/1975 | Bardani |
| 4,535,773 A | 8/1985 | Yoon |
| 5,487,739 A * | 1/1996 | Aebischer ............... C12N 11/04 604/890.1 |
| 7,344,519 B2 | 3/2008 | Wing et al. |
| 7,374,551 B2 | 5/2008 | Liang et al. |
| 7,479,150 B2 | 1/2009 | Rethy et al. |
| 2001/0003149 A1 | 6/2001 | Utterberg et al. |
| 2005/0064046 A1 | 3/2005 | DiTrolio |

(Continued)

FOREIGN PATENT DOCUMENTS

WO    WO-9601132 A1 *  1/1996  ......... A61B 17/3496

OTHER PUBLICATIONS

Chew, Stephen, Basic Laparoscopic Techniques and Advanced Endoscopic Suturing: a Practical Guidebook, 2001, Singapore University Press/World Scientific, p. 19 (Year: 2001).*

(Continued)

*Primary Examiner* — Scott J Medway
*Assistant Examiner* — Dung T Ulsh
(74) *Attorney, Agent, or Firm* — Kerr IP Group, LLC

(57) ABSTRACT

A method of atraumatic medication pellet delivery using an atraumatic trocar apparatus is described. The atraumatic trocar apparatus includes a cannula and an obturator. The method includes receiving the obturator by the cannula, wherein the obturator passes through the interior passage and exits through the anterior cannula opening so that the obturator anterior rounded tip extends past the anterior cannula end and at least one opening proximate to the anterior rounded tip also extends past the anterior cannula end. The method includes inserting the atraumatic insertion trocar through an incision into subcutaneous tissue along an insertion path to an insertion length. Additionally, the method includes inserting one or more medication pellet into the medication slot of the inserted cannula and delivering the medication pellet(s) through the interior passage of the cannula to a subcutaneous delivery site by inserting the delivery obturator into the posterior opening of the cannula.

13 Claims, 9 Drawing Sheets

(56) References Cited

U.S. PATENT DOCUMENTS

Figure 1A:
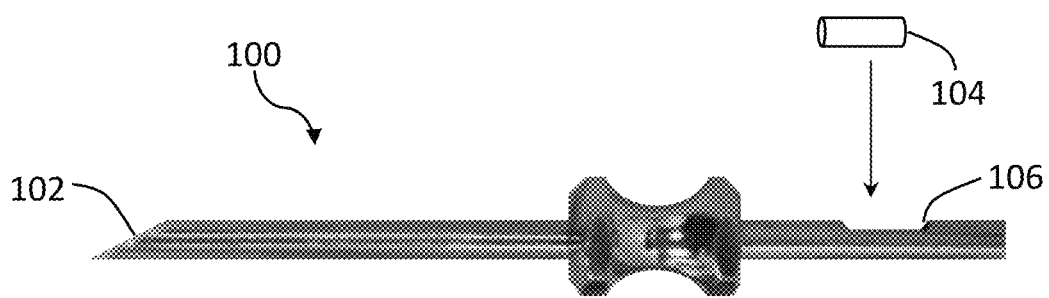

| | | | |
|---|---|---|---|
| 2005/0203565 | A1 | 9/2005 | Rethy et al. |
| 2006/0063962 | A1 | 3/2006 | Drobnik et al. |
| 2006/0282042 | A1 | 12/2006 | Walters et al. |
| 2008/0009792 | A1 | 1/2008 | Henniges et al. |
| 2008/0033280 | A1 | 2/2008 | Lubock et al. |
| 2009/0131908 | A1 | 5/2009 | McKay |
| 2012/0253189 | A1* | 10/2012 | Burbank .............. A61K 49/006 600/431 |
| 2013/0261596 | A1 | 10/2013 | McKay |
| 2014/0323808 | A1 | 10/2014 | Evans |
| 2014/0324090 | A1* | 10/2014 | Kafiluddi ........... A61B 17/3401 606/186 |
| 2016/0175007 | A1 | 6/2016 | Valbuena et al. |
| 2016/0296739 | A1 | 10/2016 | Cleveland |
| 2017/0049972 | A1* | 2/2017 | Persons ............... A61M 5/3297 |
| 2017/0065805 | A1* | 3/2017 | Tutera ............... A61M 37/0069 |
| 2018/0085144 | A1 | 3/2018 | McGillicuddy |

OTHER PUBLICATIONS

Trocar Kits, Insertion Procedure, 2015, website url: https://www.trocarkit.com/pages/insertion-procedure, accessed on Sep. 13, 2019 (Year: 2015).*

Department of Health and Human Services, Food and Drug Administration (FDA), 510(k) premarket notification for InterLock TroCar, (Jan. 9, 2017).

ISA/US, International Search Report and Written Opinion for PCTUS1919031, dated May 31, 2019, 9 pages.

* cited by examiner

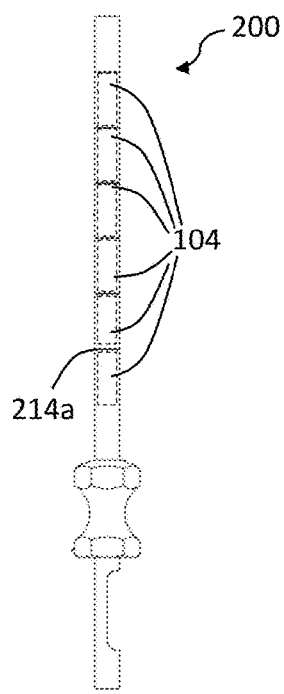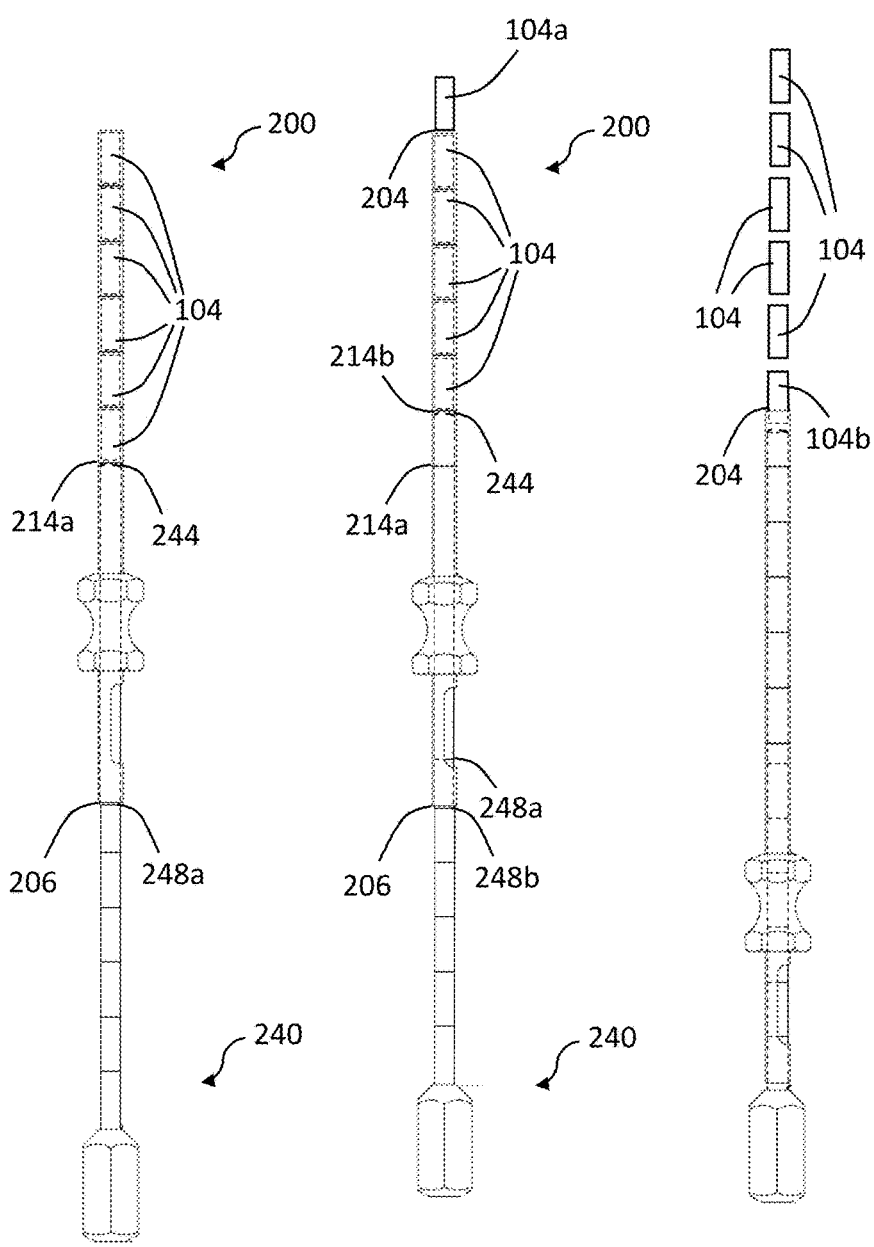
Figure 4A  Figure 4B  Figure 4C  Figure 4D

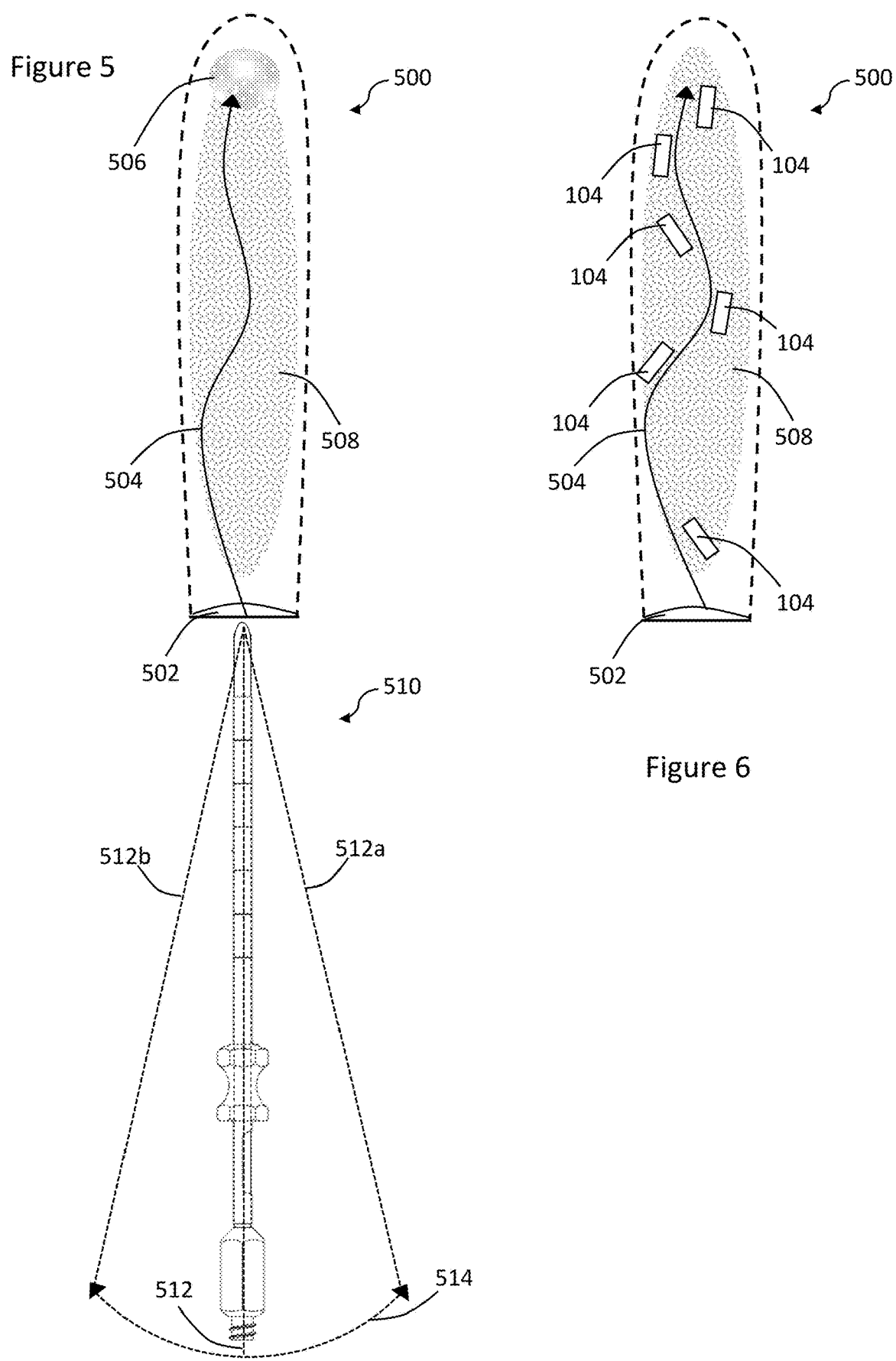

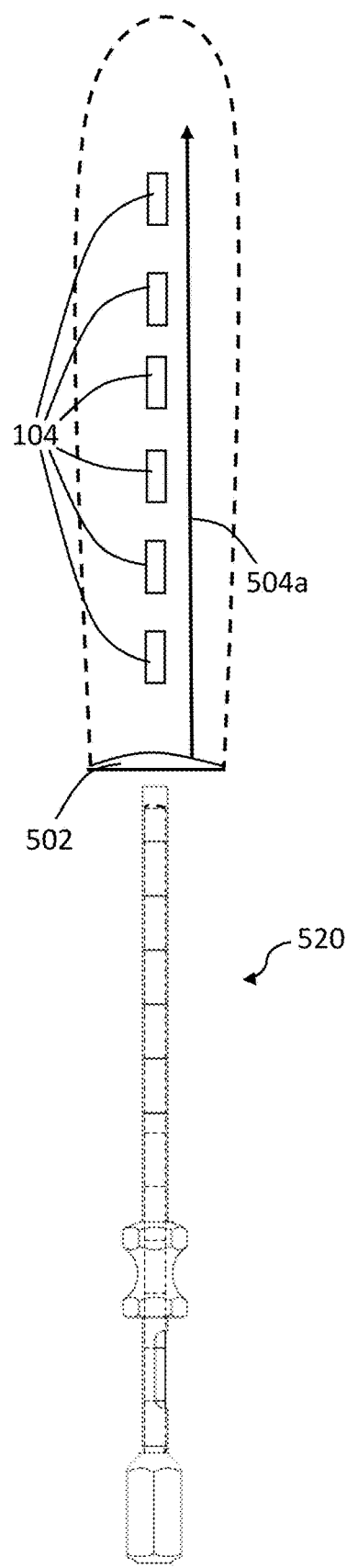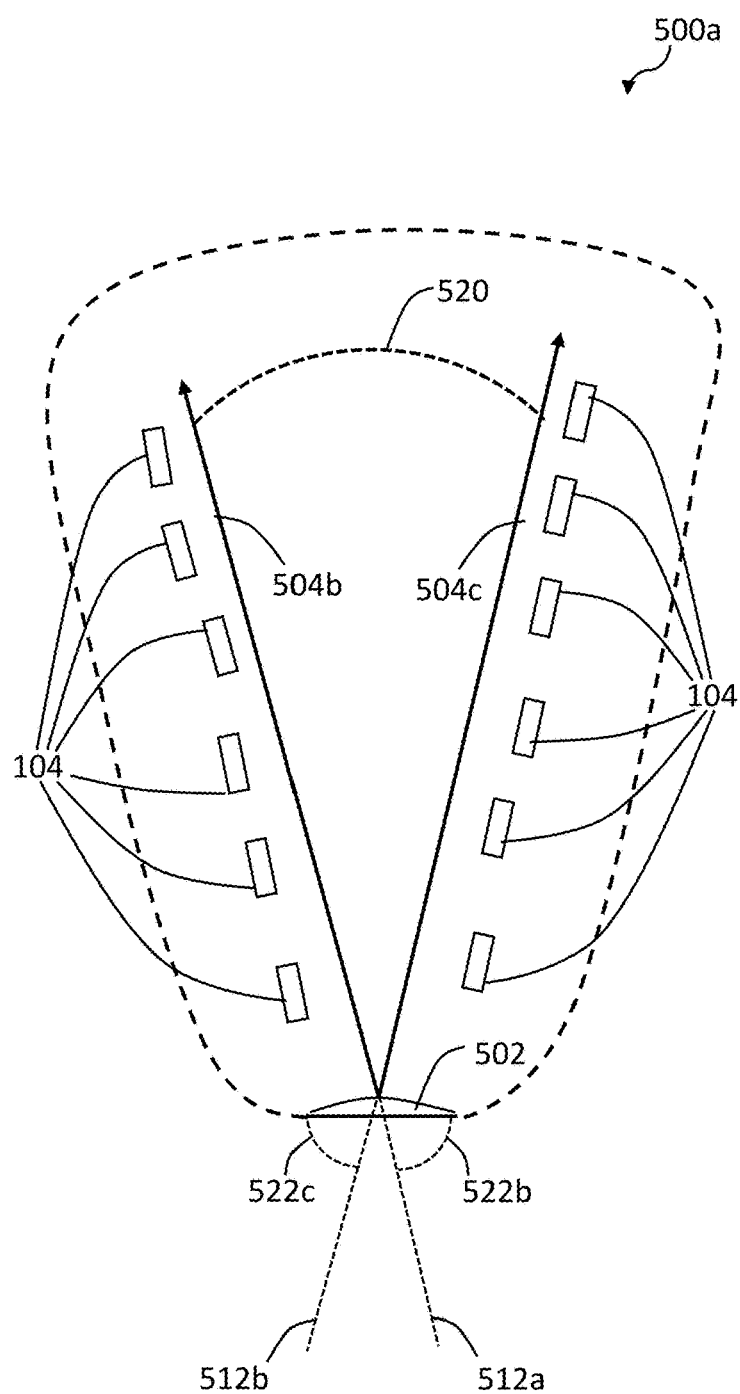
Figure 7
Figure 8

ATRAUMATIC TROCAR MEDICATION DELIVERY METHOD

FIELD

The present disclosure relates to a method for utilizing an atraumatic trocar for medication delivery. More particularly, a method for utilizing an atraumatic trocar to deliver one or more medication pellets to a subcutaneous insertion site with minimal trauma and scarring.

BACKGROUND

Hormone therapies carry significant risks of adverse effects, which can be exacerbated from inconsistent delivery of a variety of hormone therapies. Pills may be forgotten by a patient and require relatively frequent pharmacy trips to refill prescriptions. Patches may be unsightly, inconvenient, uncomfortable, removed too early, and fail to accommodate individuals requiring higher levels of hormone replacement. Creams may similarly be unsightly and inconvenient, as well as delivering inadequate levels of hormones and requiring repeated application. Injections require repeated and frequent trips to a doctor's office, and can be painful. Additionally, pill/oral, patch, cream, and injection therapies suffer inconsistent dosage delivery. Dosages of the various hormones delivered by these techniques tend to spike soon after injection, ingestion, or application, then taper quickly below efficacious medication levels.

Hormone therapies that utilize subcutaneous implants or "pellets" bypass the liver, do not affect clotting factors and do not increase the risk of thrombosis. For example, bioidentical testosterone delivered subcutaneously by pellet implant is cardiac protective, unlike oral, synthetic methyltestosterone. Subcutaneous pellets have other practical advantages over patches, creams, and injections. Subcutaneous implants release medication consistently for months, freeing patients from frequent trips to the doctor as with injections, and eliminating adherence concerns typical with patient administered medications, such as creams and oral medications. Alternatively, implants or pellet therapy keeps hormone levels consistent through the day and avoids rollercoaster-like effects from orally administered, topically administered, or injected hormones. The release of the drug from implanted pellets may continue for a period of 3 to 6 months depending on the size and composition of the pellet.

Subcutaneously implanted hormone pellets may be smaller than a grain of rice and are implanted into the subcutaneous tissue, where they provide a slow continuous release of hormone(s) into the bloodstream. Typically, the pellets are implanted in the lower abdomen or buttocks. The procedure is done in a physician's office with the use of a local anesthetic and a small incision for insertion of a trocar.

Trocar medical devices are commonly used to subcutaneously implant the hormone pellets. Trocar medical devices have been known to and used by physicians since at least the $19^{th}$ century and commonly comprise a hollow tubular cannula and a rod-like obturator that fits snugly within the cannula. A wide variety of trocars exist. These trocars vary according to the medical purpose for which they are intended; trocars are tailored for specific tasks, such as laparoscopic surgery or implant delivery.

Figure 1B:
Figure 1C:

With reference now to FIGS. 1A-C, there are shown the components of a prior art trocar apparatus for subcutaneous pellet insertion used in BIOTE® hormone replacement therapy. This prior art embodiment, includes a beveled cutting edge formed from the beveled orifice 102 of the cannula 100 and the beveled tip 112 of the insertion obturator 110. The insertion obturator 110 is machined to fit within the cannula 100 when assembled into a trocar, such that the beveled tip 112 of the insertion obturator 110 is flush with the beveled orifice 102 of the cannula 100, forming a uniform cutting edge.

As the trocar is inserted into a small surface incision, the beveled cutting edge is used to slice through the fatty and connective tissues impeding the passage of the trocar. Once inserted to a desired depth or insertion length, the insertion obturator 110 is removed from the cannula 100 and pellet(s) 104 are loaded into the cannula through a loading slot 106. A delivery obturator 120 is then used to push the pellet(s) 104 through the beveled orifice 102 of the cannula 100.

Figure 1D:
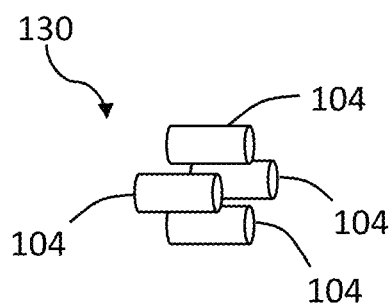
Figure 1E:
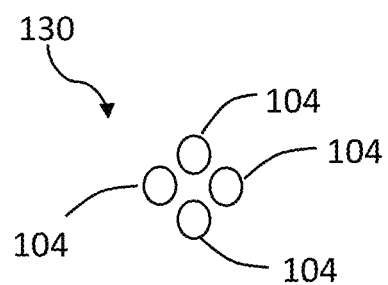

The delivery obturator 120 delivers the pellet(s) to a subcutaneous site. The beveled orifice 102 facilitates delivery of multiple pellets 104 in a clumped orientation. With reference now to FIGS. 1D and 1E, a radial clump of pellets 130 is shown. This radial clump 130 is formed by rotating the cannula during extrusion/delivery of the pellets 104 from the beveled orifice 102.

The body's primary response to the traumatic cutting insertion of the prior art beveled trocar results in inflamed tissue, lymph fluid, and clotted red blood cells. And the literature from the prior art systems teach that the inflammatory response triggered by traumatic trocar insertion of hormone pellets is critical to adequate hormone absorption.

However, prior art traumatic trocar insertion is painful and results in scarring. Additionally, traumatically inserted pellets may lead to infection and often pass outside the body, which requires replacement with an additional traumatic insertion. Furthermore, the body's inflammatory response to the traumatic insertion causes patients significant pain in the days following insertion. Further still, the cutting and spearing motions used to insert beveled trocars cause significant bruising immediately after insertion that lasts for days or weeks, and further cause scarring that may remain for a year or more. Further yet, this inflammatory response increases the healing time of the incision, and increases the probability that one or more pellets may extrude due to external pressures (falling on, sitting on, or bumping the insertion region) or internal pressures (strenuous exercise or muscle contraction).

All of these traumatic trocar insertion concerns are amplified particularly for male testosterone replacement therapy, which requires large gauge trocars and high quantities of implanted pellets. The large trocar gauge and high dosage causes a corresponding amount of pain, scarring, and risk of pellet extrusion.

Therefore, it would be beneficial to provide an apparatus, system, and method of subcutaneous pellet delivery that causes little or no trauma to the subcutaneous tissue.

SUMMARY

A method for atraumatic subcutaneous medication delivery is described. The method includes inserting an atraumatic trocar through an incision. The atraumatic trocar is inserted into a subcutaneous tissue. The atraumatic trocar includes a cannula and an insertion obturator. The cannula includes a tubular cannula body having an anterior cannula end with an anterior cannula opening and a posterior cannula end with a posterior cannula opening. The tubular cannula body includes an interior passage disposed between the posterior cannula end and the anterior cannula end. A medication slot is disposed along a portion of the tubular cannula body and is proximate to the posterior cannula end.

The insertion obturator includes a posterior insertion obturator opening, a tubular insertion obturator body and an anterior rounded tip that includes at least one opening proximate to the anterior rounded tip.

The insertion obturator is received by the posterior cannula opening and passes through the interior passage. Also, the insertion obturator passes through the anterior cannula opening so that the insertion obturator anterior rounded tip extends past the anterior cannula end. Additionally, the insertion obturator opening proximate to the anterior rounded tip extends past the anterior cannula end.

The insertion obturator and the cannula are then used to probe along an insertion path that is inserted up to an insertion length in the subcutaneous tissue. The insertion obturator is then removed from the cannula, which remains in the subcutaneous tissue.

At least one medication pellet is then placed in the cannula medication slot. A delivery obturator is then received by the posterior cannula opening. The delivery obturator includes a cylindrical shaft and an anterior blunt tip at the end of the cylindrical shaft. The medication pellet passes through the inner passage of the cannula when a push force is applied to the delivery obturator so that the anterior blunt tip of the delivery obturator pushes the medication pellet through the interior passage of the cannula. The delivery obturator enables the medicinal pellet to the exit through the anterior cannula opening and into the subcutaneous tissue.

In one illustrative embodiment, the method continues with the insertion obturator being received by the cannula and the subcutaneous tissue is probed in a side-to-side pattern.

In another illustrative embodiment, at least two or more medication pellets are then delivered to the subcutaneous tissue by passing the delivery obturator through the interior passage of the cannula. By way of example and not of limitation, a first medication pellet is placed in the medication slot and the delivery obturator pushes the first medication pellet into the cannula interior passage so that the medication slot is configured to receive a second medication pellet. A push force is then applied to the delivery obturator so that the second medication pellet enters the interior passage of the cannula.

In yet another illustrative embodiment, the two or more medication pellets are aligned along the insertion path, wherein the insertion path is linear, so that the two or more medications are inserted along a linear path.

In still another illustrative embodiment, after inserting the medication along the linear path, the subcutaneous tissue receiving the medication pellets orients the medication pellets along a non-linear path.

In another embodiment, the cannula includes a cannula handle fixedly coupled to the cannula. Additionally, the insertion obturator includes an insertion obturator handle fixedly coupled to the insertion obturator.

In yet another illustrative embodiment, the posterior cannula end includes a notch and the insertion obturator includes at least one tab that interfaces with the notch. By way of example and not of limitation, the notch at the posterior cannula end interfaces with the insertion obturator tab to prevent the insertion obturator from rotating about the cannula.

FIGURES

The presently disclosed subject matter will be more fully understood by reference to the following drawings which are presented for illustrative, not limiting, purposes.

Figure 2A:
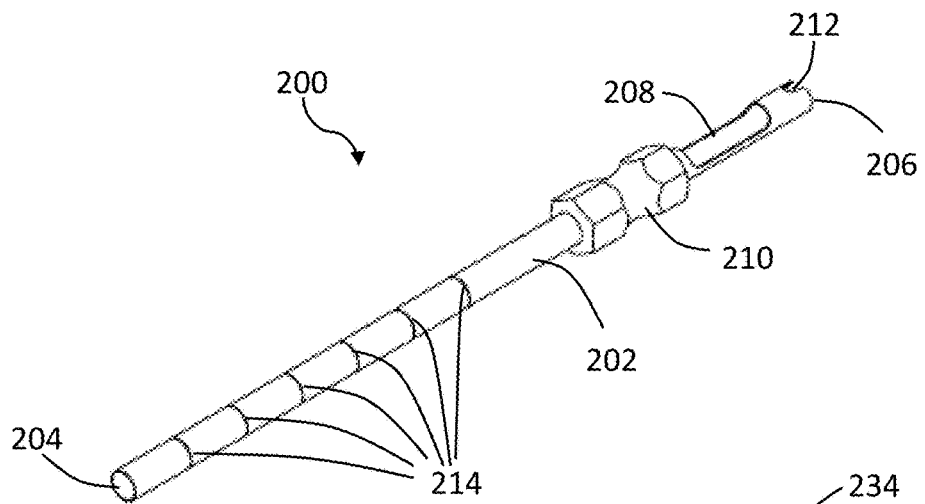
Figure 2B:
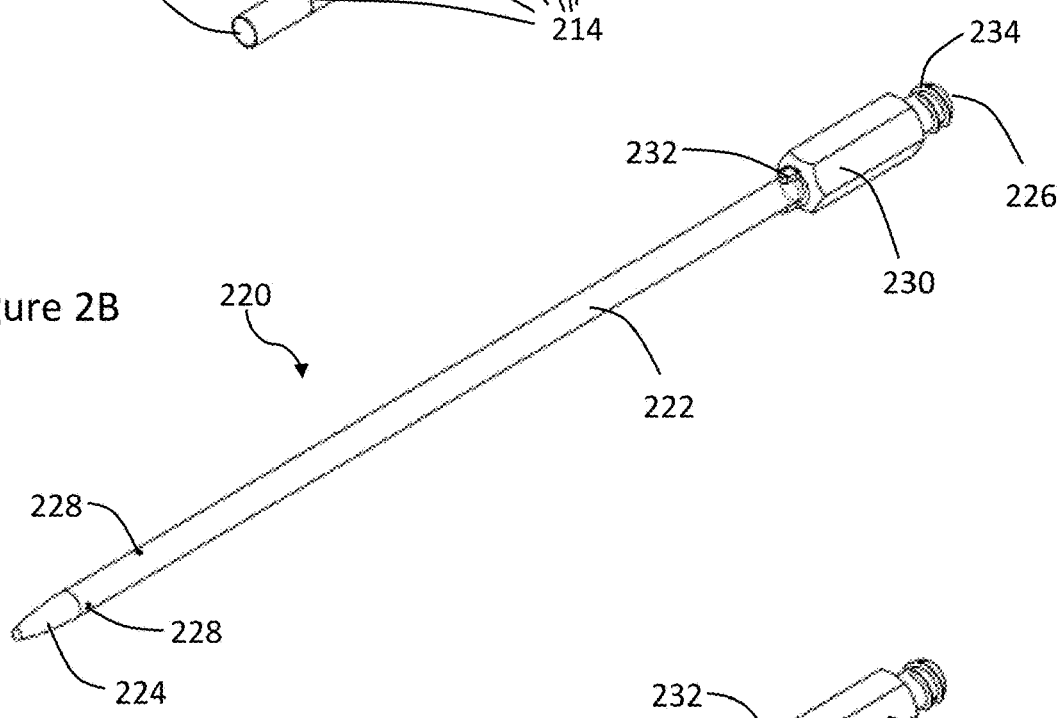
Figure 2C:
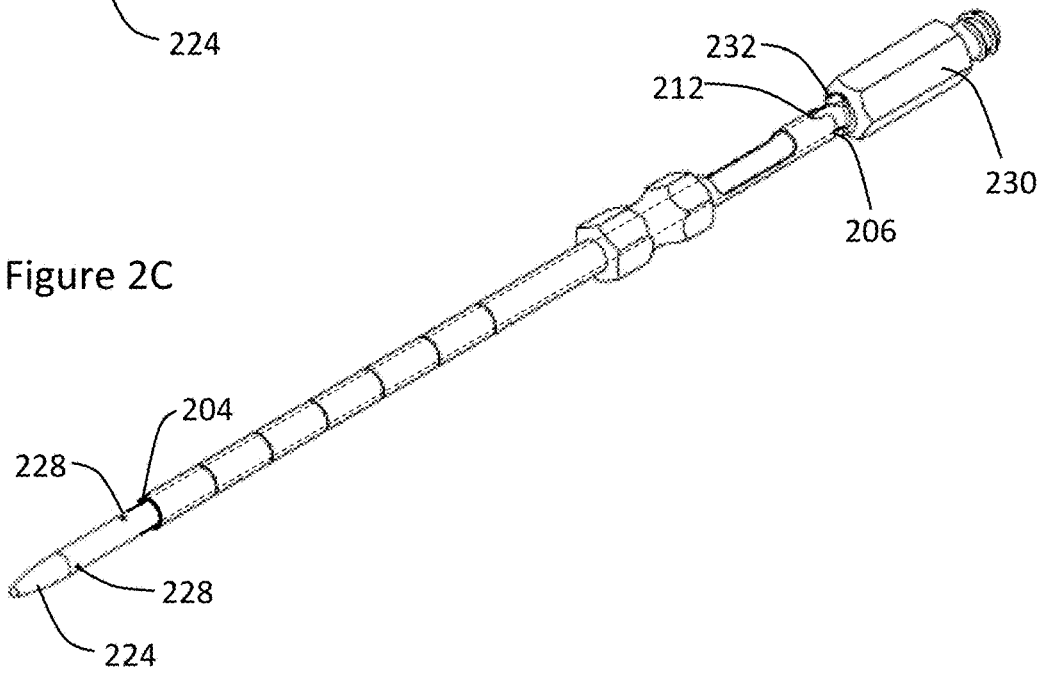
Figure 3A:
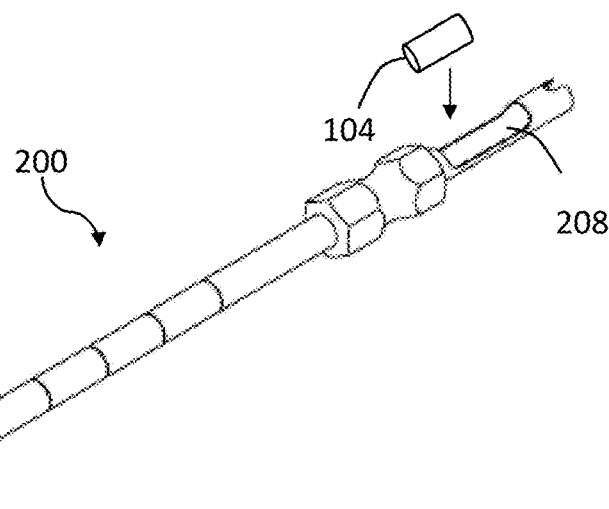
Figure 3B:
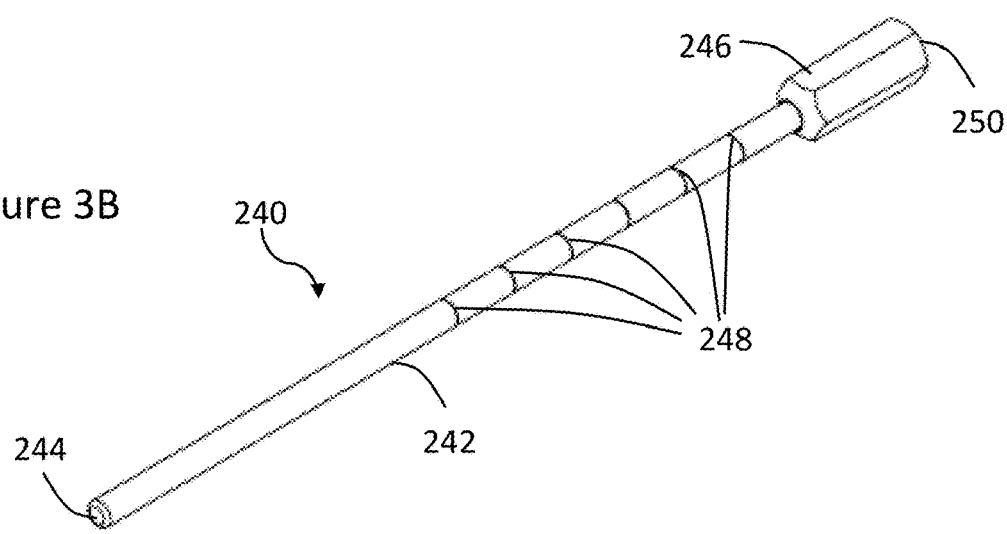
Figure 3C:
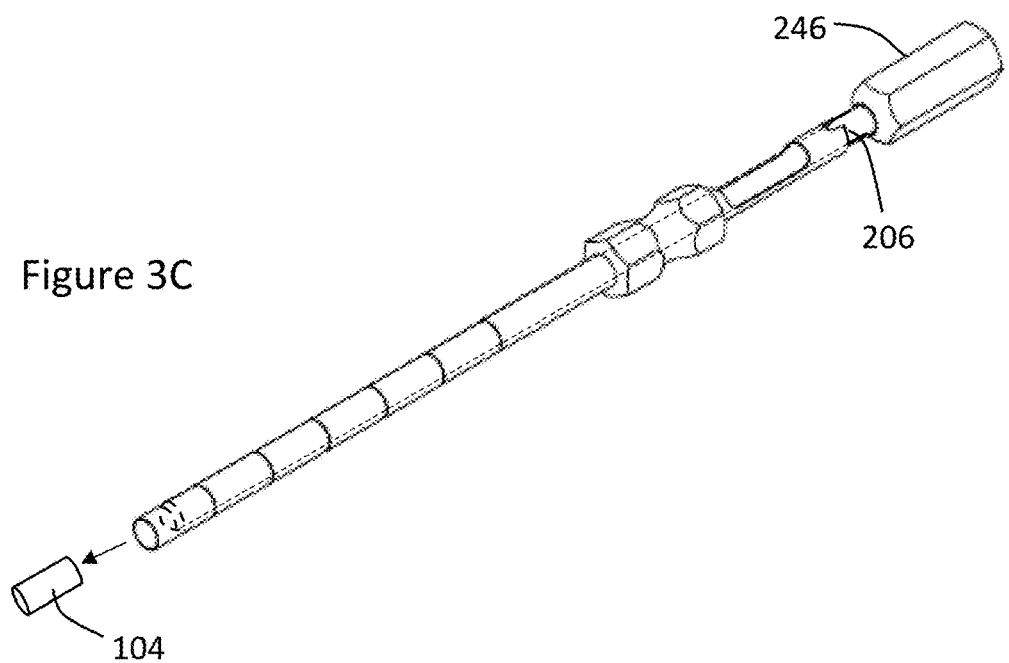
Figure 9A:
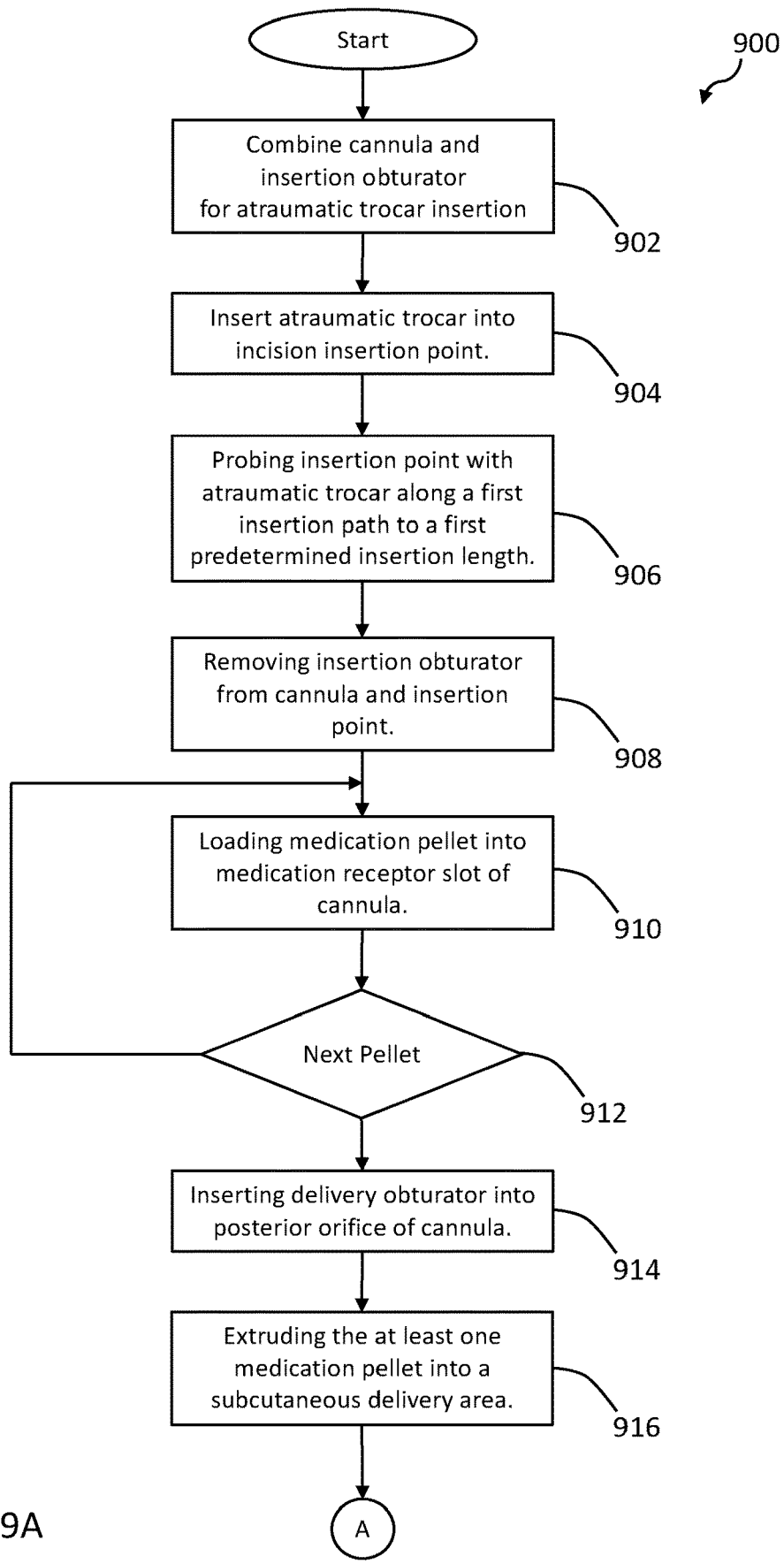
Figure 9B:
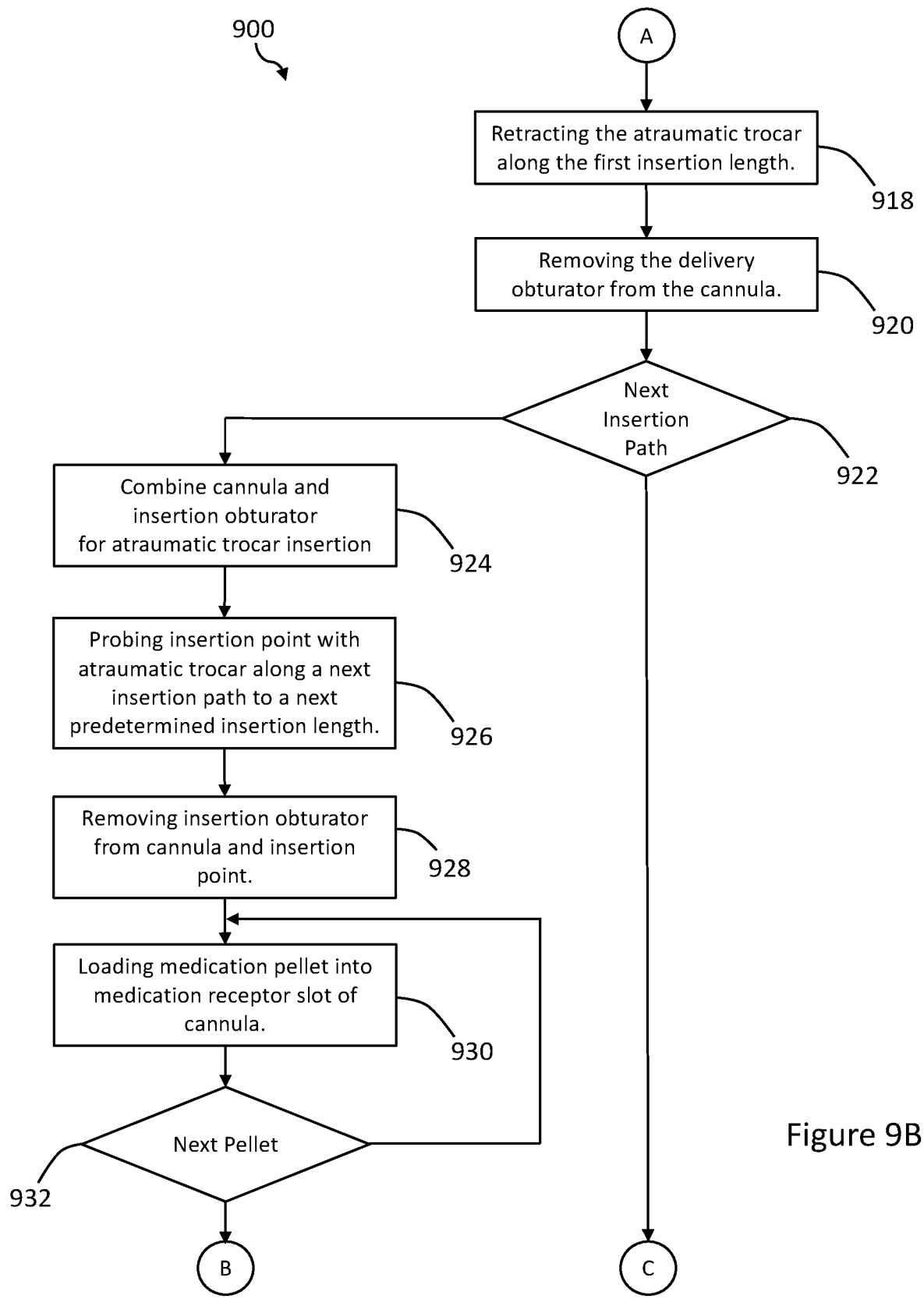
Figure 9C:
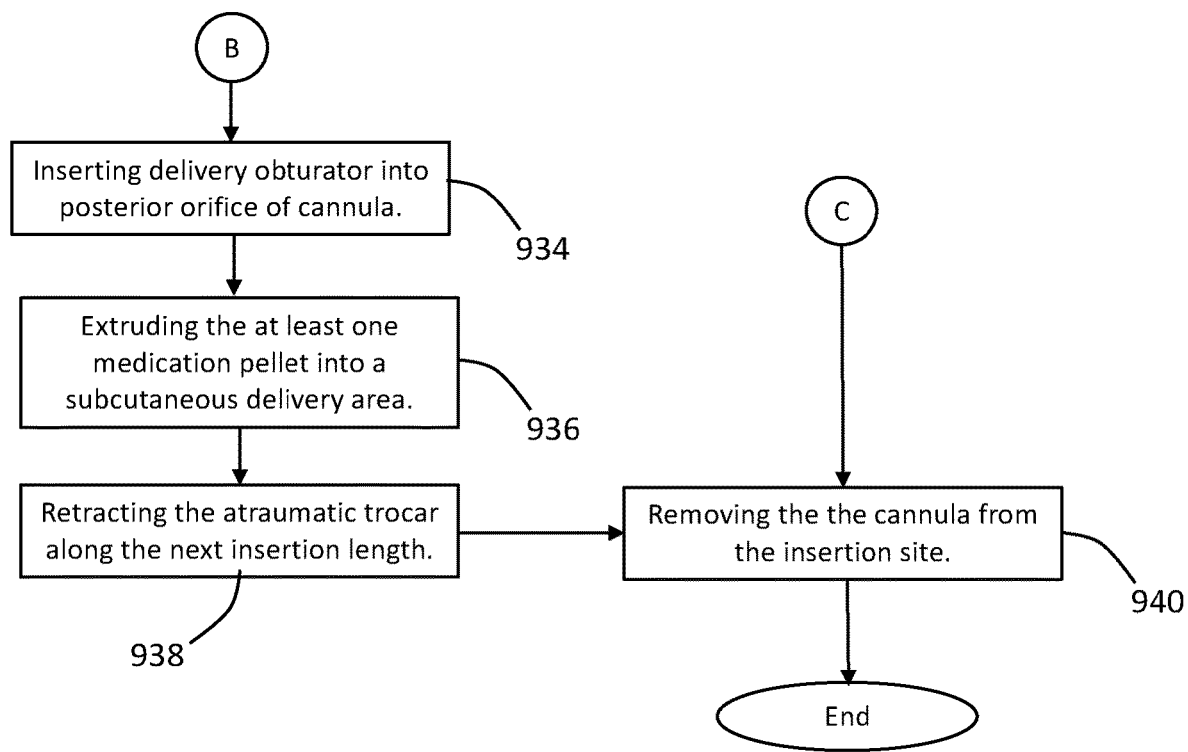

FIG. 1A shows a prior art trocar cannula.
FIG. 1B shows a prior art trocar insertion obturator.
FIG. 1C shows a prior art trocar delivery obturator.
FIG. 1D shows a side view of a prior art radial pellet clump.
FIG. 1E shows a front view of a prior art radial pellet clump.
FIG. 2A shows a perspective view of a cannula.
FIG. 2B shows a perspective view of an insertion obturator.
FIG. 2C shows a perspective view of the insertion obturator placed within the interior passage of the cannula.
FIG. 3A shows a perspective view of the cannula receiving a medication pellet.
FIG. 3B shows a perspective view of a delivery obturator.
FIG. 3C shows a perspective view of the delivery obturator placed within the interior passage of the cannula so that the delivery obturator delivers a medication pellet.
FIG. 4A shows a side view of the illustrative cannula loaded with medication pellets and the delivery obturator immediately prior to displacement and delivery of the medication pellets.
FIG. 4B shows a side view of the illustrative cannula loaded with medication pellets and the delivery obturator inserted into the cannula and pushing the medication pellets into one another and up to an anterior opening of the cannula.
FIG. 4C shows a side view of the illustrative cannula loaded with medication pellets and the delivery obturator inserted into the cannula and pushing the medication pellets into one another so that a first medication pellet is displaced.
FIG. 4D shows a side view of the illustrative delivery obturator fully inserted into the cannula and the pellets fully displaced and delivered as disclosed herein.
FIG. 5 shows a cut-away view of an illustrative delivery area, assembled insertion trocar, and side-to-side atraumatic subcutaneous probing techniques.
FIG. 6 shows a cut-away view of an illustrative staggered orientation of atraumatic subcutaneously inserted pellets.
FIG. 7 shows a cut-away view of an illustrative orientation of atraumatic subcutaneously inserted pellets and assembled delivery trocar.
FIG. 8 shows a cut-away view of an illustrative orientation of two groups of atraumatic subcutaneously inserted pellets.
FIGS. 9A-9C show an illustrative atraumatic subcutaneous pellet insertion method.

DESCRIPTION

Persons of ordinary skill in the art will realize that the following description is illustrative and not in any way limiting. Other embodiments of the claimed subject matter will readily suggest themselves to such skilled persons having the benefit of this disclosure. It shall be appreciated by those of ordinary skill in the art that the apparatus, systems and methods described herein may vary as to configuration and as to details. The following detailed description of the illustrative embodiments includes reference to the accompanying drawings, which form a part of this application. The drawings show, by way of illustration, specific embodiments in which the invention may be practiced. It is to be understood that other embodiments may be utilized and structural changes may be made without departing from the scope of the claims.

The apparatus, systems and methods described herein are used to insert an illustrative medication pellet into subcutaneous tissue. The illustrative medication pellet may be used for hormone replacement and for other applications that would require a relatively slow and sustained release of a particular medication. For purposes of this patent, the term "medication" or "medicinal" includes, but is not limited to, hormones, hormone therapy, pain medication, and other such drugs. More specifically, the term "medication" may be used to refer to drugs such as testosterone, estradiol (estrogen), fentanyl, lidocaine and other such drugs. By way of example and not of limitation, "medication" may refer to hormones, opioids and numbing agents. Additionally, the term "medication" may refer to pellet form medicine that blocks receptors in the brain, which aid in the treatment of addictive disorders including, but not limited to, alcohol and narcotics.

With respect to hormone therapy, synthetic, bioidentical, or natural hormones may be used to supplement endogenous hormones naturally produced in the human body. The illustrative apparatus, systems, kits, and methods disclosed herein pertain to the use of medication implants or "pellets." The term "pellet" is used generally to describe both medication pellets and/or hormone implants. Pellets may be small, custom compounded therapies for symptoms that stem from hormonal imbalances or are intended to manage hormone levels.

The pellets described herein may be used for hormone therapies such as menopause and low testosterone. During menopause, individuals experience symptoms including hot flashes, sleep disturbances, and night sweats. Sufferers of low testosterone experience chronic fatigue, loss of muscle mass, increased body fat (especially in the waist area), decreased bone mass, mood changes, lower mental capacity, depression, brain fog, and irritability. Testosterone helps regulate heart function, and plays a part in sperm production, bone health, energy levels, concentration, and muscle mass. Most men experience a natural decline in testosterone as they age, creating a large market for testosterone replacement therapy.

As used herein, the term "hormones" may also refer to synthetic hormones, bioidentical hormones and natural hormones. Synthetic hormones frequently do not have the same structure as endogenous hormones. Synthetic hormones may mimic the effects of endogenous hormones on many biological pathways, but they rarely offer the same effectiveness across all biological pathways. Bioidenticals are exact structural replicas of endogenous hormones, and are reported to have much lower incidences of side effects as compared to synthetic hormones. Bioidentical hormones may be derived from plants, such as soy or wild yams. Bioidentical hormones are sometimes defined as molecules identical to a hormone produced by the human body. Natural hormones are those produced in nature by various organisms, and similar to bioidenticals, are identical to a hormone produced by the human body.

An atraumatic trocar apparatus, system, kit and method are described herein. The atraumatic trocar apparatus includes a cannula, an insertion obturator and a delivery obturator. The cannula includes a tubular cannula body having an anterior cannula end with an anterior cannula opening. The cannula also includes a medication slot disposed along a portion of the tubular cannula body. As described herein, the insertion obturator is received by the cannula and passes through the interior passage of the cannula and exits through the anterior cannula opening. The insertion obturator has a rounded anterior tip and openings near the anterior tip, which is configured to delivery numbing agents before insertion of the medication pellets. The delivery obturator is used to deliver the medication pellets to the subcutaneous insertion site.

Referring to FIG. 2A, FIG. 2B and FIG. 2C there is shown an illustrative atraumatic trocar apparatus that includes an illustrative cannula and an illustrative insertion obturator. More specifically, FIG. 2A shows an illustrative embodiment of a cannula 200 having a tubular cannula body 202. The tubular cannula body 202 includes an anterior cannula opening 204 located at an anterior end of the cannula 200. The anterior end of the cannula 200 includes a blunt or rounded cylindrical end, which limits the trauma to surrounding tissue during subcutaneous implant procedure. The tubular cannula body 202 further includes a posterior cannula opening 206 located at a posterior end of the cannula 200. The tubular cannula body 202 is hollow, providing a passage through the cannula 200 and connecting the anterior cannula opening 204 to the posterior cannula opening 206. Thus, the tubular cannula body 202 includes an interior passage disposed between the posterior cannula end 206 and the anterior cannula end 204.

In the illustrative embodiment, the cannula 200 further includes a slot 208 on a portion of the tubular cannula body 202. The slot 208 is configured or sized to receive a medication pellet and thereby allow the medication access to the interior passage of the cannula 200. The slot 208 may be located proximate to the anterior cannula end.

By way of example and not of limitation, the illustrative medication pellets embodiments presented herein may include a male 200 mg testosterone pellets that has a 13 mm length and a 4 mm diameter. Additionally, an illustrative female 87.5 mg testosterone pellet has a 10 mm length and 3 mm diameter. Furthermore, the medication pellet may also include estrogen, which is delivered as a tablet having a 3 mm diameter. Thus, the "male" cannula may be sized for 4 mm medication pellets for male hormone replacement therapy and the "female" cannula may be sized for 3 mm medication pellets.

The illustrative cannula 200 may further include a cannula handle 210 fixedly coupled to the tubular cannula body 202. The cannula handle 210 may be permanently affixed to the exterior of the tubular cannula body 202, such as by welding, or removably affixed to the tubular cannula body 202, such as by threading or chemical means. Further, the tubular cannula body 202 and the cannula handle 210 may be machined from a single piece.

By way of example and not of limitation, each of the components of the atraumatic trocar apparatus, system and kit may be formed from metallic compounds, metal alloys, plastic materials, polymers or other such materials. The material properties may depend the atraumatic trocar being disposable or reusable. For example, a reusable atraumatic trocar apparatus may be composed of a stainless steel material that can be disinfected in an autoclave. A disposable atraumatic trocar may be composed of a plastic material that is intended for single use and disposal.

The illustrative cannula 200 may further include an illustrative notch 212 located at the posterior end of the tubular cannula body 202. In the illustrative embodiment, the notch 212 is triangular in shape and configured to interface with a tab on an obturator inserted into the interior passage of the cannula 200, as described below. In a further embodiment, the illustrative cannula 200 may include a second notch (not shown) in a second position at the posterior end of the tubular cannula body 202.

The illustrative cannula 200 may further include one or more cannula markings 214 along the tubular cannula body 202. In various embodiments, the cannula markings 214 are visible on the exterior of the tubular cannula body 202. Visibility of the cannula markings 214 may be achieved by scoring, embossing, raising, or coloring. Coloring may include paint, ink, anodizing, or other similarly permanent and visible techniques suitable for use in sterile operations. Where the cannula markings 214 are not scored, embossed, or raised, the cannula markings 214 may be flush with the exterior of the tubular cannula body 202. The cannula markings 214 correspond to a medication length, and serve to aid a doctor or assistant in determining the number of medications or amount of medications administered through the cannula 200.

By way of example and not of limitation, the cannula markings 214 may be scored on the surface of an illustrative stainless steel cannula. Alternatively, for a plastic cannula, the cannula markings may be embodied as raised bars on the exterior of the cannula body.

More generally, the illustrative cannula 200 has a length that may range from thirteen (13) centimeters up to seventeen (17) centimeters. The cannula length is measured from the anterior cannula opening 204 to the posterior cannula opening 206. More specifically and by way of example and not of limitation, the illustrative tubular cannula body is composed of stainless steel and has an outer diameter 0.219 inches and an inner diameter of 0.199 inches; thus, the wall thickness of the tubular cannula body is 0.010 inches. Additionally, the illustrative tubular cannula body has a length of 6.07 inches.

Referring now to FIG. 2B, there is shown an illustrative embodiment of an insertion obturator 220 having a tubular insertion obturator body 222, an anterior rounded tip 224, and a posterior insertion obturator opening 226. The tubular insertion obturator body 222 is hollow from the anterior rounded tip 224 to and through the posterior insertion obturator opening 226. By way of example and not of limitation, the illustrative insertion obturator has a length of 7.5 inches, an outer diameter of 0.188 inches and an inner diameter 0.168 inches; thus, the wall thickness for insertion obturator is 0.010 inches.

The illustrative insertion obturator 220 may further include one or more openings 228 located along the tubular insertion obturator body 222 and proximal to the anterior rounded tip 224. The openings 228 form a passage from the exterior of the tubular insertion obturator body 222 to the interior of the tubular insertion obturator body 222. In various embodiments, the openings 228 may also be located on and about the anterior rounded tip 224. By way of example and not of limitation, the openings are approximately 0.040 inches and there are six openings proximate to the anterior rounded tip 224.

The illustrative insertion obturator 220 may further include an insertion obturator handle 230 fixedly coupled to the tubular insertion obturator body 222. The insertion obturator handle 230 may be permanently affixed to the exterior of the tubular insertion obturator body 222, or removably affixed to the tubular cannula body 202, such as by threading or chemical means.

Further still, the illustrative insertion obturator 220 may include a tab 232 configured to interface with the notch 212 on the posterior end of the cannula 200. The tab 232 may be located adjacent to the insertion obturator handle 230 and may be located on the exterior surface of the insertion obturator tubular body 222. The tab 232 may be raised above the exterior surface of the insertion obturator tubular body 222. The tab 232 is fixedly coupled to one of the insertion obturator handle 230 and the insertion obturator tubular body 222. In various embodiments, the tab 232 and the insertion obturator handle 230 are formed from a single machined piece. In some embodiments, the insertion obturator 220 includes a second tab 233 located at a second position about the exterior surface of the insertion obturator tubular body 222.

The insertion obturator 220 may further include a threaded posterior end 234. The threaded posterior end 234 may be configured to receive a medication from a syringe pump. By way of example and not of limitation, the threaded posterior end 234 includes a luer lock receptor, which is configured to interface with plastic tubing that delivers a numbing solution. The numbing solution may include saline, lidocaine and epinephrine.

More generally, the illustrative insertion obturator 220 has a length that may range from eighteen (18) centimeters up to twenty-two (22) centimeters. The insertion obturator length is measured from the anterior point of the anterior rounded tip 224 to the posterior insertion obturator opening 226.

Referring now to FIG. 2C, there is shown the illustrative insertion obturator 220 inserted into the interior passage of the illustrative cannula 200, in which the portion of the insertion obturator tubular body 222 within the interior passage of the cannula 200 is shown with dotted lines.

In one embodiment, the insertion obturator 220 is long enough in comparison to the cannula 200, that the rounded tip 224 and at least one opening 228 protrude beyond the anterior end of the cannula 200 and through the anterior cannula opening 204 when the insertion obturator 220 is inserted into the cannula 200 so that the tab 232 interfaces with the notch 212.

In other embodiments, the insertion obturator 220 is long enough in comparison to the cannula 200, that the rounded tip 224 and at least one opening 228 protrude beyond the anterior end of the cannula 200 and through the anterior cannula opening 204 when the insertion obturator 220 is inserted into the cannula 200 so that the insertion obturator handle 230 abuts the posterior cannula end.

By way of example and not of limitation, the outer diameter of the insertion obturator is 0.188 inches and the inner diameter of the cannula is 0.199 inches; thus, there is approximately a gap of 0.005 inches between the inner diameter of the cannula and the outer diameter of the insertion obturator.

With reference now to FIG. 3A, there is shown an illustrative cannula 200 receiving a medication pellet at the medication slot 104. The received medication pellet resides within the interior passage of the cannula 200. By way of example and not of limitation, the medication slot 104 is 0.56 inches and is configured to received a 0.5 inch medication pellet.

Referring now to FIG. 3B, there is shown an illustrative delivery obturator 240 having a cylindrical shaft 242 and an anterior blunt tip 244. The illustrative delivery obturator 240 may further include a delivery obturator handle 246 affixed to the cylindrical shaft 242.

In the illustrative embodiment, the anterior cannula end is blunt and in combination with the blunt tip of the delivery obturator 240 forms a blunt surface. In the illustrative embodiment, the blunt surface includes rounded or beveled edges of the anterior end of the cylindrical shaft. The combination of the anterior cannula end and the blunt tip 244 of the delivery obturator 240 are blunt or rounded to reduce or prevent instances of tissue tearing during subcutaneous pellet procedure.

In the illustrative embodiment, the delivery obturator handle 246 is located at a posterior end of the delivery obturator 240. The illustrative delivery obturator 240 may further include one or more delivery markings 248 along the cylindrical shaft 242. In various embodiments, the delivery markings 248 are visible on the exterior of the cylindrical shaft 242. Visibility of the delivery markings 248 may be achieved by scoring, embossing, or coloring. Coloring may include paint, ink, anodizing, or any suitable flush marking technique. Where the delivery markings 248 are not recessed or scored, the delivery markings 248 may be flush with the exterior of the cylindrical shaft 242. The illustrative delivery markings 248 correspond to a medication length of 0.5 inches, and serve to aid a surgeon or assistant in determining the number of medications or amount of medications administered through the cannula 200 with the delivery obturator 240. In a further embodiment, the delivery markings 248 correspond to the cannula markings 214, which are also 0.5 inches.

More generally, the illustrative delivery obturator 240 has a length that may range from sixteen (16) centimeters up to twenty (20) centimeters. The delivery obturator length is measured from the anterior blunt tip 244 to a posterior end 250 of the delivery obturator 240.

Referring now to FIG. 3C, there is shown the illustrative delivery obturator 240 inserted into the interior passage of the illustrative cannula 200 such that at least one medication pellet 104 passes through the anterior opening of the cannula 200. The portion of the delivery obturator cylindrical shaft 242 within the interior passage of the cannula 200 is shown with dotted lines. The delivery obturator 240 is long enough in comparison to the cannula 200 that the anterior blunt tip 244 is of sufficient length to pass the medication pellet(s) through the cannula.

For example, the delivery obturator 240 may extend to within one (1) centimeter of the anterior end of the cannula 200. In this embodiment, the delivery obturator is long enough to push at least one pellet 104 to the anterior cannula opening 204, such that a portion of the at least one pellet 104 protrudes through the anterior cannula opening 204.

In another embodiment, the delivery obturator 240 is long enough in comparison to the cannula 200 that the anterior blunt tip 244 is flush with the anterior end of the cannula 200 and the anterior cannula opening 204 when the delivery obturator 240 is inserted into the cannula 200 to a maximum allowable extent. The maximum allowable extent is the point at which the delivery obturator handle 246 abuts the posterior cannula opening 206 and the posterior end of the cannula 200.

The atraumatic trocar apparatus described above may be embodied in a kit that includes the cannula 200, the insertion obturator 220, the delivery obturator 240 and an outer package that houses the cannula, insertion obturator and delivery obturator. By way of example and not of limitation, the illustrative atraumatic trocar kit may also include a scalpel, scissors, bandages, antiseptic ointments, and other such materials that may be used during the medical procedure.

With reference now to FIG. 4A, there is shown an illustrative cannula 200 loaded with several medication pellets 104 and an illustrative delivery obturator 240 positioned near the cannula 200 in preparation to deliver the medication pellets by extrusion through the cannula 200. The length from the most posterior marking 214a on the cannula 200 to the posterior cannula opening 206 and posterior end of the cannula 200 corresponds to the length from the anterior blunt tip 244 to the most anterior marking 248a on the delivery obturator.

Referring now to FIG. 4B, the delivery obturator 240 is inserted into the interior passage of the cannula 200 so that the most anterior marking 248a on the delivery obturator 240 are adjacent to the posterior cannula opening 206. The portion of the delivery obturator 240 that is within the interior passage of the cannula 200 is represented by dotted lines. In this configuration, the blunt tip 244 of the delivery obturator 240 pushes the medication pellets 104 into positions in the interior passage of the cannula 200 corresponding to the cannula markings 214.

Referring now to FIG. 4C, the delivery obturator 240 is inserted into the interior passage of the cannula 200 so that the second most anterior marking 248b on the delivery obturator 240 is adjacent to the posterior cannula opening 206. When the delivery obturator 240 is inserted into the interior passage of the cannula 200 to such a length, the most anterior marking 248a on the delivery obturator 240 is disposed within the interior passage of the cannula 200, the blunt tip 244 of the delivery obturator 240 is aligned with the second most posterior marking 214b of the cannula 200; and the medication pellet 104a passes through the anterior opening 204 of the cannula 200 and delivered.

With reference now to FIG. 4D, the delivery obturator 240 is inserted into the interior passage of the cannula 200 to the full length of the delivery obturator 240, where the delivery obturator handle 246 abuts the posterior opening 206 of the cannula 200. In this configuration, the medication pellets 104 are extruded and delivered even though a portion of the most posterior medication pellet 104b remains within the interior passage of the cannula 200. A portion of the most posterior medication pellet 104b remains within the interior passage of the cannula 200 because this illustrative delivery obturator embodiment has a length that does not extend the blunt tip 244 of the delivery obturator 240 up to or through the anterior opening 204 of the cannula 200 at the anterior end of the cannula 200. The portion of the most posterior medication pellet 104b remaining within the interior passage of the cannula 200 is represented by dotted lines, while the portion of the most posterior medication pellet 104b that has been extruded from or through the anterior opening 204 of the cannula 200 is represented by solid lines.

Referring now to FIG. 5, there is shown an illustrative insertion area 500 and assembled atraumatic insertion trocar 510 having a centerline 512. The insertion area 500 is demarcated by the dotted line representing the boundary of an internal cavity surrounding subcutaneous tissue, and includes an incision site 502, an insertion path 504, a delivery site 506, and a delivery area 508. The assembled atraumatic insertion trocar 510 follows the insertion path 504 to the delivery site 506 by angling the centerline 512 along an arc 514 during insertion from a right centerline extreme 512a to a left centerline extreme 512b, repeatedly.

With reference now to FIG. 6, there are shown medication pellets 104 delivered subcutaneously in the delivery area 508 through the incision site 502 from a cannula 200 inserted along the illustrative insertion path 504. The swerving and curving insertion path 504 allows an assembled atraumatic insertion trocar to slip past various connective and fatty tissues without causing trauma, creating a linear space for the cannula 200. Upon removal of the cannula 200 during medication pellet 104 delivery, the connective and fatty tissues return toward their original position and pushing the delivered medication pellets 104 askew and effectively locking the medication pellets 104 in place in the subcutaneous tissue.

Referring now to FIG. 7, there are shown medication pellets 104 delivered through the incision site 502 along a linear insertion path 504a and an assembled atraumatic delivery trocar 520.

With reference to FIG. 8, there is shown an insertion area 500a containing two sets of delivered medication pellets 104, wherein the medication pellets 104 are delivered along separate insertion paths 504c and 504b. The separate insertion paths 504a and 504b are separated by an angular distance 520 corresponding to the angle 522c or 522b at which the centerline 512a and 512b of the assembled atraumatic insertion trocar (not shown) was inserted into the incision site 502 and the assembled atraumatic delivery trocar 520 was removed.

Referring now to FIGS. 9A-9C, there is shown an atraumatic method of subcutaneous medication delivery 900. The method begins at step 902 by combining the cannula 200 and insertion obturator 220 to form the atraumatic insertion trocar 510. The rounded tip 224 of the insertion obturator 220 is inserted into the posterior cannula opening 206, through the interior passage of the cannula 200, so that the rounded tip 224 extends out through the anterior cannula opening 204. In a further embodiment, the insertion obturator 220 is inserted into the posterior cannula opening 206 so that the tab 232 on the insertion obturator 220 interfaces with the notch 212 on the tubular cannula body 202, and causes the assembled atraumatic insertion trocar 510 to rotate about the centerline 512 as a single unit, i.e. rotating the insertion obturator handle 230 causes the cannula 200 to rotate the same amount, and rotating the cannula handle 210 causes the insertion obturator 220 to rotate the same amount as well.

At step 904 the assembled atraumatic insertion trocar 510 is inserted into the incision site 502 that is also termed an insertion site. The anterior rounded tip 224 of the insertion obturator 220 and thus, the assembled atraumatic insertion trocar 510, enters the incision 502 or insertion site, followed by the remaining portions of the atraumatic insertion trocar 510 as described further below.

At step 906 the incision 502 or insertion point is probed with the assembled atraumatic insertion trocar 510 along an insertion path to a predetermined insertion length. The insertion path may be linear, angled, or oscillating. FIG. 7 demonstrates a linear insertion path 504a, FIG. 8 demonstrates angled insertion paths 504b and 504c, and FIGS. 5 and 6 demonstrate an oscillating insertion path 504. an insertion path may only be angled with respect to another insertion path passing through the same incision 502 or insertion site as the first insertion path. An oscillating insertion path may be achieved by directing the posterior portion of the assembled atraumatic insertion trocar 510 in a side-to-side fashion. The side-to-side motion operates to pass the rounded tip 224 around and past connective tissues in the subcutaneous tissue.

In operation, a doctor or assistant gently pushes the assembled atraumatic insertion trocar 510 along an insertion path, moving the posterior portion of the assembled atraumatic insertion trocar 510 to one side or the other as the doctor or operator feels resistance from connective tissues impeding the passage of the atraumatic insertion trocar 510 along the insertion path. The predetermined length to which the insertion path is probed may be measured by observing the deformation or bulging of the outer dermis layer caused by the passage of the atraumatic insertion trocar 510 passing through the subcutaneous tissue. In other embodiments, the predetermined length may be measured using the cannula markings 214. Using the cannula markings 214 ensures that the insertion length is sufficient that the loaded medication pellets 104 are deposited within the subcutaneous tissue or to ensure that the medication pellets 104 are deposited a desired distance from the incision 502 or insertion site.

In one embodiment, one or more numbing solutions are administered through openings 228 in the anterior portion of the insertion obturator 220 while the assembled atraumatic insertion trocar 510 probes along the insertion path. By way of example and not of limitation, the numbing solution may include a combination of a saline solution, lidocaine and epinephrine; the numbing agent is lidocaine and the epinephrine constricts the blood vessels to minimize bleeding.

At step 908, the insertion obturator 220 is removed from the cannula 200 and the incision 502 or insertion site. In one embodiment, the cannula 200 is kept in position, while the insertion obturator 220 is removed. The cannula 200 may be kept in position by holding the cannula handle 210 while the insertion obturator handle is used to remove the insertion obturator 220.

At step 910, a medication pellet 104 is loaded into the interior passage of the cannula 200 through the medication slot 208. In one embodiment, the loaded medication pellet is pushed toward the anterior opening 204 at the anterior end of the cannula 200 with the delivery obturator 240, but not through the anterior opening 204.

At decision diamond 912, a next medication pellet may be loaded into the interior passage of the cannula 200 in the same fashion as the first medication. The next medication pellet 104 can be a second, third, fourth, fifth, sixth, etc. medication pellet depending on the number of previously loaded medication pellets. In one embodiment, when a next pellet is loaded into the interior passage of the cannula 200, the most recently loaded medication pellet is pushed toward the anterior opening 204 at the anterior end of the cannula 200 with the delivery obturator 240. However, unlike the initially loaded medication pellet, any next or subsequently loaded medication pellets are pushed so that none of the previously loaded medication pellets is extruded through the anterior opening 204 at the anterior end of the cannula 200 and delivered to a delivery area 508.

At step 914, the desired number of medication pellets 104 have been loaded into the interior passage of the cannula 200, and the blunt tip 244 of the delivery obturator 240 is inserted into the posterior opening 206 of the cannula 200. The blunt tip 244 of the delivery obturator 240 is passed through the interior passage of the cannula 200 to abut the most posterior loaded medication pellet 104 and push all pellets into a desired position. In one embodiment, the desired position for the medication pellets is as depicted in FIG. 4B, where the loaded pellets 104 pressed to abut one another and align with the cannula markings 214, as well as the anterior opening 204 of the cannula 200.

At step 916, the loaded medication pellet(s) 104 are extruded through the anterior opening 204 of the cannula 200 and delivered to a subcutaneous delivery area 508. In one embodiment, the cannula 200 is slowly removed from the incision 502 as the delivery obturator 240 is inserted further into the interior passage of the cannula 200. By slowly removing the cannula 200 during insertion of the delivery obturator 240, the delivery site 506 for each successively delivered medication pellet is shifted closer to the incision 502 or insertion site. Moving the delivery site 506 allows the medication pellets to be delivered in a linear formation as in FIG. 7, or a snaking, winding or "staggered" formation as in FIG. 6.

At step 918, the assembled atraumatic delivery trocar 520 is retracted along the insertion path toward the incision 502 or insertion site. In one embodiment, at least an anterior portion of the cannula 200 remains within the incision 502 or insertion site.

At step 920, the delivery obturator 240 is removed from the cannula 200. At decision diamond 922, a doctor or assistant may determine whether to proceed with a second or next insertion or whether to begin terminating the method. If termination is elected, the method proceeds to step 940. If a second or next insertion is elected, the method proceeds to step 924.

At step 924, the method proceeds by again combining the cannula 200 and the insertion obturator 220 to form the atraumatic insertion trocar 510. Since at least an anterior portion of the cannula 200 remains within the incision 502 or insertion site, when the insertion obturator 220 is inserted into the interior passage of the cannula the rounded tip 224 emerges from the anterior opening 204 of the cannula 200 directly into subcutaneous tissue within the incision 502 or insertion site. In a further embodiment, the insertion obturator 220 is inserted into the posterior cannula opening 206 so that the tab 232 on the insertion obturator 220 interfaces with the notch 212 on the tubular cannula body 202.

At step 926, the assembled insertion trocar 510 is angled away from the previous insertion path, as with the insertion paths 504b and 504c in FIG. 8, towards a next or second insertion path. The assembled insertion trocar 510 is then used to probe along the length of the next or second insertion path to a predetermined insertion length. As with the initial insertion path, the second insertion path linear or oscillating, but must be angle away from the initial insertion path.

At step 928, as with step 908, the insertion obturator 220 is removed from the cannula 200 and the incision 502 or insertion site, while keeping the cannula 200 in place within the incision 502 or insertion point.

At step 930, as with step 910, a medication pellet 104 is loaded into the interior passage of the cannula 200 through the medication slot 208. In one embodiment, only one medication pellet is loaded into the medication slot.

At decision diamond 932, as with decision diamond 912, a next medication pellet may be loaded into the interior passage of the cannula 200 in the same fashion as the first medication pellet, or the method may proceed to step 934.

At step 934, as with step 914, the desired number of medication pellets 104 have been loaded into the interior passage of the cannula 200, and the blunt tip 244 of the delivery obturator 240 is inserted into the posterior opening 206 of the cannula 200. The blunt tip 244 of the delivery obturator 240 is passed through the interior passage of the cannula 200 to abut the most posterior loaded medication pellet 104 and push all pellets into a desired position.

At step 936, as with step 916, the loaded medication pellet(s) 104 are extruded through the anterior opening 204 of the cannula 200 and delivered to a second subcutaneous delivery area.

At step 938, as with step 918, the assembled atraumatic delivery trocar 520 is retracted along the insertion path toward the incision 502 or insertion site. In one embodiment, at least an anterior portion of the cannula 200 remains within the incision 502 or insertion site, allowing the method to either terminate at step 940 or return to decision diamond 922.

At step 940, the cannula 200 or assembled atraumatic delivery trocar 520 is removed from the incision 502 or the insertion site; the incision 502 is closed and the method ends.

The atraumatic trocar apparatus, system and method described above may be used to deliver medication pellets into subcutaneous tissue without damaging the subcutaneous tissue. The inventor hypothesizes that the atraumatic insertion and subcutaneous delivery of medication pellets improves the absorption rate of the medication pellets over prior art trocar apparatuses by limiting or eliminating injury, such as laceration to nerves, arterioles, venuoles, capillaries, or fat cell membrane injury, which results in cellular death and formation of chronic collagenous scar tissue.

The inventor further hypothesize that the atraumatic insertion and subcutaneous delivery of medication pellets allows the incision, made to insert the medication pellets, to heal more quickly and decrease the likelihood that a subcutaneously delivered or inserted medication pellet is inadvertently extruded from the subcutaneous tissue because of pressure, a fall, or other stress.

Additionally, the inventor hypothesizes that the reduced inflammation caused by the atraumatic trocar apparatus and methods reduces the degree and incidence of scarring at the incision site.

Furthermore, the inventor hypothesizes that the atraumatic method of pushing aside and slipping past connective and fatty tissue with the rounded tip of the insertion obturator allows the connective and fatty tissue to move or pop back toward their original position as the delivery trocar is removed from the insertion path and incision. As the connective and fatty tissue moves, slides, or pops back toward its original position, the connective and fatty tissues have the effect of locking or blocking the delivered medication pellets in place.

Further still, the inventor hypothesizes that the locking or blocking action of the connective and fatty tissue prevents or limits the likelihood that the delivered medication pellets are inadvertently extruded from the subcutaneous tissue because of pressure, a fall, or other stress.

It is to be understood that the detailed description of illustrative embodiments are provided for illustrative purposes. Thus, the apparatus, system, kit and method presented above may evolve to benefit from the improved performance and lower cost of the future hardware components that meet the system and method requirements presented. The scope of the claims is not limited to these specific embodiments or examples. Therefore, various process limitations, elements, details, and uses may differ from those just described, or be expanded on or implemented using technologies or materials not yet commercially viable, and yet still be within the inventive concepts of the present disclosure. The scope of the invention is determined by the following claims and their legal equivalents.

What is claimed is:

1. A method for delivering two or more medication pellets through an incision to a delivery site within a subcutaneous tissue comprising:

receiving an obturator in a tubular cannula body, wherein the obturator includes an anterior rounded tip, a tubular obturator body, a first coupling element, and at least one opening proximate to the anterior rounded tip, wherein the cannula includes the tubular cannula body having an anterior end and a posterior end, a second coupling element disposed along a portion of the tubular cannula body, and a medication slot disposed along the tubular cannula body, wherein a surface of the anterior end of the tubular cannula body includes a smooth edge;

passing the obturator through the tubular cannula body so that the anterior rounded tip of the obturator, the at least one opening proximate to the anterior rounded tip, and a portion of the tubular obturator body extend past the anterior end of the tubular cannula body when the first coupling element and the second coupling element couple to one another;

probing, with the cannula and the obturator, the incision into the subcutaneous tissue along an insertion path within the subcutaneous tissue up to an insertion length;

removing the obturator from the tubular cannula body;

placing the two or more medication pellets in the medication slot;

receiving, by the tubular cannula body, the obturator;

passing, by the anterior rounded tip of the obturator, the two or more medication pellets through the tubular cannula body so that the obturator pushes the two or more medication pellets through the tubular cannula body and the two or more medication pellets exit the tubular cannula body;

delivering, by passing the obturator through the tubular cannula body, the two or more medication pellets, wherein a first medication pellet of the two or more medication pellets is placed in the medication slot and the obturator pushes the first medication pellet into the tubular cannula body so that a second medication pellet of the two or more medication pellets is received in the medication slot; and aligning the first medication pellet and the second medication pellet along the insertion path, wherein the insertion path includes the two or more medication pellets oriented along a non-linear path.

2. The method of claim 1 further including probing along the insertion path in a side-to-side pattern the cannula and the obturator, so that the anterior rounded tip of the obturator precedes the cannula.

3. The method of claim 1 wherein the cannula includes a cannula handle fixedly coupled to the cannula; and the obturator includes an obturator handle fixedly coupled to the obturator.

4. The method of claim 1 wherein the second coupling element includes at least one notch, and the first coupling element includes at least one tab.

5. The method of claim 1 wherein the obturator includes a posterior threading surrounding a posterior obturator opening, wherein the posterior threading is configured to interface with a tubing.

6. A method for delivering two or more medication pellets through an incision to a delivery site within a subcutaneous tissue, the method comprising:

inserting an atraumatic trocar through the incision to the delivery site within the subcutaneous tissue, wherein the atraumatic trocar includes, a cannula with a tubular cannula body, wherein a surface of an anterior end of the tubular cannula body includes a smooth edge, and wherein the cannula is formed with a medication slot disposed along the tubular cannula body at a location more proximate to a posterior end of the tubular cannula body than the anterior end, wherein the posterior end of the tubular cannula body includes a first coupling element disposed along a portion of the tubular cannula body, and the medication slot receives the two or more medication pellets, an obturator that includes a tubular obturator body, an anterior rounded tip, at least one opening proximate to the anterior rounded tip of the obturator, and a second coupling element, and wherein the obturator is configured to be received within the tubular cannula body, and extend through the tubular cannula body so that the anterior rounded tip of the obturator, the at least one opening proximate to the anterior rounded tip, and an anterior portion of the tubular obturator body extend past the anterior end of the tubular cannula body when the first coupling element and the second coupling element couple to one another;

probing, with the atraumatic trocar, the incision along an insertion path up to an insertion length;

removing the obturator from the cannula;

placing the two or more medication pellets in the medication slot of the cannula;

receiving, by the tubular cannula body, the obturator; and passing, by the anterior rounded tip, the two or more medication pellets through the tubular cannula body so that the anterior rounded tip pushes the two or more medication pellets through the tubular cannula body and the two or more medication pellets exit the tubular cannula body into the subcutaneous tissue;

delivering, by passing the obturator through the tubular cannula body, the two or more medication pellets, wherein a first medication pellet of the two or more medication pellets is placed in the medication slot and the obturator pushes the first medication pellet into the tubular cannula body so that the medication slot receives a second medication pellet of the two or more medication pellets; and aligning the first medication pellet and the second medication pellet along the insertion path, wherein the insertion path includes the two or more medication pellets oriented along a non-linear path.

7. The method of claim 6 further including probing, with the atraumatic trocar, in a side-to-side pattern.

8. The method of claim 6 wherein the cannula further includes a cannula handle fixedly coupled to the cannula; and the obturator further includes an obturator handle fixedly coupled to the obturator.

9. The method of claim 6 wherein the second coupling element includes at least one notch, and the first coupling element includes at least one tab.

10. The method of claim 6 wherein the obturator further includes a posterior threading surrounding a posterior obturator opening, wherein the posterior threading is configured to interface with a tubing.

11. A method for delivering two or more medication pellets through an incision to a delivery site within a subcutaneous tissue, the method comprising:

inserting an atraumatic trocar through the incision to the delivery site within the subcutaneous tissue, wherein the atraumatic trocar includes, a cannula with a tubular cannula body, wherein a surface of an anterior end of the tubular cannula body includes a smooth edge, and wherein the cannula is formed with a medication slot disposed along the tubular cannula body at a location more proximate to a posterior cannula end than an anterior cannula end, wherein the posterior end of the tubular cannula body includes a first coupling element disposed along a portion of the tubular cannula body, and the medication slot receives the two or more medication pellets, a cannula handle fixedly coupled to the tubular cannula body, an obturator that includes a tubular obturator body, an anterior rounded tip, and at least one opening proximate to the anterior rounded tip of the obturator, an obturator handle fixedly coupled to the obturator, wherein the obturator handle includes a second coupling element and a threaded posterior end surrounding an obturator handle opening, wherein the threaded posterior end of the obturator handle is configured to interface with a tubing,
receiving the obturator in the tubular cannula body, and
passing the obturator through the tubular cannula body so that the anterior rounded tip of the obturator, the at least one opening proximate to the anterior rounded tip, and an anterior portion of the tubular obturator body extend past the anterior cannula end when the first coupling element and the second coupling element couple to one another;
probing with the atraumatic trocar along an insertion path up to an insertion length;
removing the obturator from the cannula;
placing the two or more medication pellets in the medication slot;
receiving the obturator within the tubular cannula body;
passing the two or more medication pellets through the tubular cannula body when a force is applied to the obturator so that the anterior rounded tip of the obturator pushes the two or more medication pellets through the tubular cannula body so that the two or more medication pellets exit through the anterior cannula end;
delivering, by passing the obturator through the tubular cannula body, at least two or more medication pellets, wherein a first medication pellet of the two or more medication pellets is placed in the medication slot and the obturator pushes the first medication pellet through the tubular cannula body so that the medication slot receives a second medication pellet of the two or more medication pellets, wherein the first medication pellet and the second medication pellet are received in the subcutaneous tissue oriented in a non-linear pattern.

12. The method of claim 11 further including probing in a side-to-side pattern the atraumatic trocar that includes the cannula and the insertion obturator.

13. The method of claim 11 wherein the second coupling element includes at least one notch, and the first coupling element includes at least one tab.

\* \* \* \* \*